United States Patent
Han et al.

(10) Patent No.: US 11,078,477 B2
(45) Date of Patent: Aug. 3, 2021

(54) AUTOMATED ISOLATION AND CHEMICAL REACTION(S) OF NUCLEIC ACIDS

(71) Applicant: BIOCHAIN INSTITUTE, INC., Newark, CA (US)

(72) Inventors: Xiaoliang Han, San Francisco, CA (US); James Jianming Wang, Newark, CA (US); Tong Lu, Newark, CA (US)

(73) Assignee: BIOCHAIN INSTITUTE, INC., Newark, CA (US)

( * ) Notice: Subject to any disclaimer, the term of this patent is extended or adjusted under 35 U.S.C. 154(b) by 0 days.

(21) Appl. No.: 16/663,212

(22) Filed: Oct. 24, 2019

(65) Prior Publication Data

US 2020/0115701 A1  Apr. 16, 2020

Related U.S. Application Data

(63) Continuation of application No. 15/432,861, filed on Feb. 14, 2017, now abandoned, which is a continuation-in-part of application No. 14/517,759, filed on Oct. 17, 2014, now abandoned.

(51) Int. Cl.
| | | |
|---|---|---|
| *C12N 15/10* | (2006.01) | |
| *G01N 1/10* | (2006.01) | |
| *C12Q 1/6806* | (2018.01) | |
| *B01L 3/00* | (2006.01) | |
| *G01N 35/00* | (2006.01) | |

(52) U.S. Cl.
CPC ...... *C12N 15/1013* (2013.01); *B01L 3/50851* (2013.01); *C12Q 1/6806* (2013.01); *G01N 1/10* (2013.01); *B01L 2300/0858* (2013.01); *G01N 35/0098* (2013.01); *G01N 2035/00564* (2013.01)

(58) Field of Classification Search
CPC .................. C12N 15/1013; B01L 3/50851
See application file for complete search history.

(56) References Cited

U.S. PATENT DOCUMENTS

| | | | | |
|---|---|---|---|---|
| 6,884,395 B2 * | 4/2005 | Tooke | ................... | B01L 3/5027 210/651 |
| 2008/0221372 A1 * | 9/2008 | Rothmann | .......... | B01L 3/50851 585/1 |
| 2008/0281087 A1 * | 11/2008 | Markert-Hahn | ..... | C12Q 1/6806 536/25.3 |
| 2009/0042290 A1 * | 2/2009 | Steele | ................ | C12N 15/1003 435/375 |
| 2011/0165565 A1 * | 7/2011 | Wang | ................... | C12Q 1/6818 435/6.11 |
| 2011/0245087 A1 * | 10/2011 | Weiss | ................... | C12Q 1/6886 506/7 |
| 2011/0262919 A1 * | 10/2011 | Tajima | ...................... | B01L 3/52 435/6.11 |
| 2013/0017544 A1 * | 1/2013 | Eckhardt | ........... | B01L 3/502792 435/6.11 |

OTHER PUBLICATIONS

DeVos et al, Circulating Methylated SEPT9 DNA in Plasma Is a Biomarker for Colorectal Cancer, 2009, Clinical Chemistry, 55, 1337-1346. (Year: 2009).*
DeVos et al, Circulating Methylated SEPT9 DNA in Plasma Is a Biomarker for Colorectal Cancer, 2009, Clinical Chemistry, 55, 1337-1346, supplemental information pp. 1-5. (Year: 2009).*

* cited by examiner

*Primary Examiner* — Narayan K Bhat
(74) *Attorney, Agent, or Firm* — Lin Sun-Hoffman; Yong Chen; Liu Chen & Hoffman LLP (57) ABSTRACT

The present teachings relate to methods, kits and devices for performing automated sequential nucleic acid isolation and conversion/purification in a single closed system. In various embodiments, the present teaching enable a user to (i) load a device with test samples, reagents and consumables; (ii) select or program the device for the desired nucleic acid isolation and subsequent chemical treatment and/or conversion reaction(s) without further user intervention; and recovering the isolated and treated and/or converted nucleic acid at the conclusion of the program once the device is activated.

8 Claims, 6 Drawing Sheets

Specification includes a Sequence Listing.

AUTOMATED ISOLATION AND CHEMICAL REACTION(S) OF NUCLEIC ACIDS

CROSS-REFERENCE TO RELATED APPLICATIONS

This application is a continuation of U.S. patent application Ser. No. 15/432,861, filed Feb. 14, 2017, which is a continuation in part of U.S. patent application Ser. No. 14/517,759, filed Oct. 17, 2014, the disclosure of each of which is incorporated herein by reference.

FIELD

The present teachings relate to methods, kits and a device for automated nucleic acid isolation and conversion/purification in a single closed system.

INTRODUCTION

Isolation of nucleic acids from biological samples provides reliable results when the nucleic acids are free of contaminating foreign nucleic acids, nucleases that degrade nucleic acids and chemicals that interfere with downstream analysis of the isolated nucleic acids. The subsequent analysis of isolated nucleic acid is at further risk for introduction of contaminants during the manual set-up of the reaction/treatment of the isolated nucleic acids. Thus, there remains a need in the art for methods and devices that facilitate the isolation and subsequent reaction/treatment of isolated nucleic acids in an automated system to preclude introduction of contaminants and interfering chemicals. The disclosed innovations address these needs.

SUMMARY OF INVENTION

In one aspect, disclosed is a method for performing sequential nucleic acid isolation and conversion/purification reaction(s) in a single closed system, wherein an isolated and converted nucleic acid is prepared for a modification detection, having mixture of reaction with a nucleic acid-containing test sample and an extraction reagent, wherein an isolated nucleic acid is obtained from the sample; reacting said isolated nucleic acid with a conversion reagent; wherein the reacted nucleic acid is converted. In some embodiments, the method is in a single closed system that is an automated system. In some embodiments, the automated system is a device or an instrument. In some embodiments, the single closed automated system is built in a device and the environment can be a sterile environment. In some embodiments, the conversion is a chemical conversion. In some embodiments, the chemical conversion is a bisulfite conversion, wherein the bisulfite conversion reagents have an over-layer of mineral oil wherein the bisulfite conversion is deamination of cytosine into uracil, wherein 5-methylcytosine is not converted. In some embodiments, a bisulfite conversion further comprises an optional step of desulfonation. In some embodiments, the modification detection is, but not limited to, a methylation detection after bisulfite conversion and/or desulfonation. In some embodiments, the reaction is a methylation of said isolated nucleic acid, wherein said nucleic acid is a control sample. In some embodiment, the automated system increase the efficiency and shorten the time for the assay. In some embodiments, the isolation and conversion/purification of the nucleic acid occurs in three and half hours and utilizes magnetic beads. In another embodiment, the assay time is at 1 hrs, 2 hrs and 3 and 3.5 hrs. In yet another embodiment, the present invention provides the reduction of volume of the sample processing. The automation has two sections—one section (A) comprises the nucleic acid isolation/extraction chamber and the other section (B) comprises the conversion/purification reaction chamber. In one embodiment, samples from section A with large volume are passed to section B becoming a smaller volume. Section A's sample volume ranges 1 ml, 2 ml, 3 ml, 4 ml, 5 ml, 6 ml, 7 ml, 8 ml, 9 ml, 10 ml, 15 ml and 20 ml. In one embodiment, volume in Section B with samples in the chamber is reduced to the ranges from 500 ul, 400 ul, 300 ul, 200 ul, 100 ul, 90 ul, 80 ul, 70 ul, 60 ul, 50 ul, 40 ul 30 ul, 20 ul, 10 ul, to 5 ul.

In some embodiments, the sample is selected from a group consisting of whole blood, plasma, serum, buffy coat, urine, tears, stool, respiratory and genitourinary tract swabs, saliva, cheek swab, sputum, cerebral spinal fluid, a formalin fixed paraffin embedded (FFPE) sample, fragments of different organs, a cell, a tissue, blood cells, circulating tumor cell (CTC) or a disseminated tumor cell (CTD), bone, samples of in vitro cell cultures and specimens that have been suspected to contain nucleic acid molecules. In some embodiments, the nucleic acid is DNA, RNA, cDNA or a combination thereof and the isolated nucleic acid is further suitable for PCR, qPCR, sequencing, restriction enzyme digestion, ligation, transfection, hybridization, genotyping, forensics testing, quality control, bisulfite reaction, methylation reaction, disease detection, prognosis, and molecular diagnosis. In some embodiments, the isolated nucleic acid can be reacted in a sequential nucleic acid reactions selected from the group consisting of an enzymatic, extension, hybridization, ligation, polyadenylation, deamination, methylation or blotting.

In some embodiments, disclosed is a method for performing sequential nucleic acid isolation and bisulfite conversion reaction to prepare for a nucleic acid modification detection, in a single closed automated system comprising: introducing a nucleic acid-containing sample into a reaction tube or a reservoir wherein said reaction tube is within a device for performing sequential nucleic acid isolation and conversion/purification in a single closed system; reacting the nucleic acid-containing sample with an extraction reagent; binding the extracted nucleic acid to magnetic beads subsequently added after the extraction reaction, wherein an isolated nucleic acid is obtained from the sample; reacting said isolated nucleic acid with a bisulfite conversion reagent, wherein the bisulfite conversion reagent has an over-layer of mineral oil; and binding the bisulfite-converted nucleic acid to magnetic beads subsequently added after the conversion reaction, wherein bisulfite-converted nucleic acid is obtained.

In some embodiments, disclosed is a method for nucleic acid extraction combined with bisulfite conversion comprising: a) contacting a sample with a first magnetic particle under conditions permissive for nucleic acid binding to said particle on an automated reaction platform, wherein DNA is bound to the first magnetic particle forming a first nucleic acid:particle complex; b) eluting the nucleic acid from the particle; c) contacting the eluted nucleic acid with a bisulfite reagent overlaid with mineral oil under conditions permissive for a bisulfite reaction to produce a converted nucleic acid within the nucleic acid; and d) eluting the bisulfite treated nucleic acid from a second magnetic particle in a second eluting step. In some embodiments, the sample is combined with a lysis binding buffer, wherein the lysis buffer is extracted from a sealed chamber positioned within a reaction platform and wherein said sample and lysis buffer are combined in a first reaction reservoir on said reaction platform at a temperature of about 40° C. for about 360 seconds. In some embodiments, prior to elution the nucleic acid:particle complex is washed with a wash solution followed by drying the complex. In some embodiments, the nucleic acid is eluted from the particle by the addition of about 100 μl elution buffer and heated to 80° C.+/−2° C. with aspiration-blow action by the transfer tip for about 10 minutes. In some embodiments, the eluted nucleic acid is transferred from the first reaction reservoir to a second reaction reservoir where contact with the bisulfite reagent includes an over layer of mineral oil on top of the bisulfite reagent and the bisulfite reaction is performed at 80° C.+/−2° C. with for about 45 min. In some embodiments, the isolation and conversion/purification of the nucleic acid occurs in less than about three and half hours. In some embodiments, the reaction is methylation, wherein cytosine is converted into 5-methyl cytosine. In some embodiments, the bisulfite conversion is deamination of cytosine into uracil, wherein 5-methylcytosine is not converted. In some embodiments, a bisulfite conversion is followed by a step of desulfonation. In some embodiments, the second eluting step is proceeded by transferring a second magnetic particle to a third reaction reservoir on said reaction platform and contacting the bisulfite treated nucleic acid with the second magnetic particle. In some embodiments, about 1000 μl wash solution is mixed with the bisulfite treated nucleic acid and the second magnetic particle, wherein DNA is bound to the second magnetic particle forming a second nucleic acid:particle complex and the complex is mixed by aspirating/blowing action for about 250 times within the third reaction reservoir and the washing may be repeated at least once. In some embodiments, the washed second nucleic acid:particle complex is dried followed by eluting the bisulfite treated nucleic acid from the second particle by the addition of about 60 μl elution buffer and reacted at 23° C.+/−2° C. with aspiration-blow action for 250 times in about 10 minutes. In some embodiment, the bisulfite treated nucleic acid is followed by a step of desulfonation. In some embodiment, the converted nucleic acid is further analyzed for modification detection, wherein the modification detection comprises, but is not limited to methylation detection. In some embodiments, the sample is selected from the group consisting of whole blood, plasma, serum, buffy coat, urine, tears, stool, respiratory and genitourinary tract swabs, saliva, cheek swab, sputum, cerebral spinal fluid, a formalin fixed paraffin embedded (FFPE) sample, fragments of different organs, a cell, a tissue, blood cells, circulating tumor cell (CTC) or a disseminated tumor cell (CTD), bone, samples of in vitro cell cultures or specimens that have been suspected to contain nucleic acid molecules. In some embodiments, the nucleic acid is DNA, RNA, cDNA or a combination thereof and the isolated nucleic acid is further suitable for PCR, qPCR, sequencing, restriction enzyme digestion, ligation, transfection, hybridization, genotyping, forensics testing, quality control, bisulfite reaction, methylation reaction, disease detection, prognosis, and molecular diagnosis. In some embodiments, the isolated nucleic acid can be reacted in a sequential nucleic acid reactions selected from the group consisting of an enzymatic, extension, hybridization, ligation, polyadenylation, deamination, methylation or blotting.

In some embodiments, disclosed is a method for performing sequential nucleic acid sample reaction(s) comprising: a) introducing a nucleic acid-containing sample into a reaction reservoir of a device for performing automated sequential nucleic acid isolation and conversion/purification in a single closed system via a pipet tip attached to the uni-directional auto sample head within said device; b) reacting the nucleic acid-containing sample with one or more reagents, wherein each reagent is transferred from its own compartment within a disposable cartridge within said device by separate pipet tips attached to the uni-directional auto sample head; c) separating the reacted nucleic acid from the reaction components; and d) eluting the reacted nucleic acid from a nucleic acid:particle complex in the reaction reservoir. In some embodiments, prior to introducing the sample into the reaction reservoir the sample is reacted with a lysis binding buffer, wherein the lysis buffer is extracted from its own compartment within the disposable cartridge, and wherein following reaction with the lysis buffer the nucleic acid is free within the buffer solution. In some embodiments, eluting the reacted nucleic acid is proceeded by binding the nucleic acid to a magnetic particle transferred from the its own compartment within the disposable cartridge, wherein a nucleic acid:particle complex is formed. In some embodiments, the complex is washed with a wash solution transferred from its own compartment within the disposable cartridge. In some embodiments, the particle within the nucleic acid:particle complex is selected from the group consisting of a magnetic particle, a magnetic bead, and a coated bead with a magnetic center. In some embodiments, the reaction reservoir is in contact with a magnet within the device, wherein the reaction reservoir is configured to the magnet. In some embodiments, steps a., b., c., and d. are repeated in succession for each sequential nucleic acid reaction, wherein a subsequent nucleic acid reaction is reacted in a second, a third, a fourth, etc. reaction reservoir within said device. In some embodiments, the sample is selected from the group consisting of whole blood, plasma, serum, buffy coat, urine, tears, stool, respiratory and genitourinary tract swabs, saliva, cheek swab, sputum, cerebral spinal fluid, a formalin fixed paraffin embedded (FFPE) sample, fragments of different organs, a cell, a tissue, blood cells, circulating tumor cell (CTC) or a disseminated tumor cell (CTD), bone, samples of in vitro cell cultures or specimens that have been suspected to contain nucleic acid molecules. In some embodiments, the nucleic acid is DNA, RNA, cDNA or a combination thereof and the isolated nucleic acid is further suitable for PCR, qPCR, sequencing, restriction enzyme digestion, ligation, transfection, hybridization, genotyping, forensics testing, quality control, bisulfite reaction, methylation reaction, disease detection, prognosis, and molecular diagnosis. In some embodiments, the isolated nucleic acid can be reacted in a sequential nucleic acid reactions selected from the group consisting of an enzymatic, extension, hybridization, ligation, polyadenylation, deamination, methylation or blotting.

In another aspect, a device is disclosed for performing automated sequential nucleic acid isolation and conversion/purification in a single closed device comprising: reaction tubes for processing and reacting a test sample; at least one, sealed cartridge containing comprising a plurality of sealed compartments containing reagents, wherein reagents have an over-layer of mineral oil, wherein said reagents are used in isolation and conversion/purification of nucleic acids from the test sample; a heating unit capable of contacting a plurality of reaction tubes, wherein each reaction tube contains at least one of the extraction reaction and the conversion reaction and a magnet configured to the reaction tubes. In some embodiments, the device further has a UV lamp, a uni-directional auto sample head, wherein said sample head is synchronized with a stage moving within said device, automated liquid handling, a plurality of reaction reservoirs and a heat block. In some embodiments, the single closed device is an automated system, is sealed from the external environment such as a closed compartment and the single closed device can be a sterile environment. In some embodiments, the isolation and conversion/purification of the nucleic acid occurs in less than three and half hours wherein the isolation and conversion/purification of the nucleic acid is a bisulfite conversion. In some embodiments, the reaction is methylation, wherein cytosine is converted into 5-methyl cytosine. In some embodiments, the bisulfite conversion is deamination of cytosine into uracil, wherein 5-methylcytosine is not converted. In some embodiments, a bisulfite conversion further comprises an optional step of desulfonation.

In yet another aspect, disclosed is a kit for use with a biological sample for extraction of nucleic acid and bisulfite conversion of the polynucleotide on an automated platform comprising reagents for extracting nucleic acid in a set of sealed reagent cartridges and reagents for reacting and extracting bisulfite treated nucleic acid in a second set of sealed reagent cartridges. In some embodiments, the kit has at least one or more of reagent that can include ethanol, tip wash buffer, Wash A buffer, magnetic beads, and lysis buffer for extracting nucleic acid and protection buffer with an over layer of mineral oil, bisulfite conversion solution with an over layer of mineral oil, Wash A buffer, magnetic beads, Wash B buffer, elution buffer and tip wash buffer.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

A better understanding of the novel features and advantages of the disclosed invention can be obtained by reference to the following description that sets forth illustrative embodiments, in which the principles of the disclosed invention are utilized, and the accompanying drawings of which.

DETAILED DESCRIPTION

The present teachings can be implemented for integrated and automated nucleic acid isolation and conversion reactions within a single closed system In some embodiments, disclosed herein are methods and systems for integrating the extraction of nucleic acid from a sample and reacting the isolated nucleic acid, within the same work-flow, in at least one conversion reaction, including but not limited to, e.g., an enzymatic digest, a bisulfite reaction, a ligation reaction, etc. Both extraction and subsequent conversion(s) reactions are performed as one process, without stopping, within a device having an automated system for transferring samples, reagents and consumables from a sealed reaction cartridge(s) containing the reagents and consumables to reaction reservoirs and reacted sample storage tubes with the device. The methods described herein can simultaneously extract nucleic acids from a plurality of samples followed by reacting the plurality of extracted nucleic acids in a conversion reaction(s) to provide reacted nucleic acids for further analysis, including but not limited to, PCR, qPCR, sequencing, and sequencing to determine disease detection, prognosis and diagnosis.

Unless otherwise specified, terms and symbols of biochemistry, nucleic acid chemistry, molecular biology, developmental biology and molecular genetics follow those of standard treaties and texts in the field, for example, Sambrook et al, Molecular Cloning: A Laboratory Manual, $2^{nd}$ Edition (Cold Spring Harbor Press, 1989); Alberts and Singer, Developmental Biology, Eighth Edition (Sinauer Associates Inc., Sunderland, Mass., 2006); Komberg and Baker, DNA Replication, Second Edition (W.H. Freeman, New York, 1992); Gaits, ed., Oligonucleotide Synthesis: A Practical Approach (IRL Press, Oxford, 1984); Lehninger, Biochemistry, Second Edition (Worth Publishers, New York, 1975); Eckstein, ed., Oligonucleotides and Analogs: A Practical Approach (Oxford University Press, New York, 1991); and the like.

The terminology used therein is for the purpose of describing particular embodiments only and is not intended to be limiting of a systems and methods of this disclosure. As used herein and in the appended claims, the singular forms "a," "an," and "the" include plural referents unless the context clearly dictates otherwise. Thus, for example, reference to "a nucleic acid" can refer to one nucleic acid sequence or to mixtures of such sequences, and reference to "the method" includes reference to equivalent steps and/or methods known to those skilled in the art, and so forth. Furthermore, to the extent that the terms "including", "includes", "having", "has", "with", or variants thereof are used in either the detailed description and/or the claims, such terms are intended to be inclusive in a manner similar to the term "comprising".

Additionally, to facilitate understanding, disclosed are a number of terms as defined herein.

The phrase, "automated system" as used herein can refer to the mechanization of a manual process in which a robotic apparatus and the like is directed by a mechanical means, e.g., a computer, a computer key card, a bar code reader able to provide operation parameters to an apparatus for performing the manual process without human intervention once the process within the automated system is engaged.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. The term "about" as used herein refers to a range that is 15% plus or minus from a stated numerical value within the context of the particular usage. For example, about 10 would include a range from 8.5 to 11.5.

The phrase "closed system" as used herein, can refer to a system separate from an external factor, such as an environmental factor, physical factor, and so on that could possibly otherwise interfere with or contaminate the operation, reaction, function as well as materials, samples, reagents and so on present within the closed system.

As used here "cartridge" as used herein, can refer to a reagent pack to deliver individual reagents or consumables (fluid and solid), each contained within a compartment within the cartridge and each reagent is sealed so as to prevent contamination from one compartment to another compartment by reagent aspiration, spill over and so on. Use of a cartridge with a plurality of sealed compartments permits delivery or acceptance of a fluid or solid while isolating the contents of the cartridge from the external environment, and protecting the user from exposure to the fluid contents.

The phrase, "sealed cartridge" as used herein, can refer to a cartridge having individual compartments in which each compartment contains a liquid or solid, reagent or consumable used within a reaction, for example, a conversion reaction, a nucleic acid extraction reaction, a PCR reaction, a qPCR reaction and so on as would be understood by one of skill in the art.

The phrase "bisulfite conversion" as used herein, can refer to the modifying, altering or otherwise changing a molecule of cytosine to uracil or keeping 5-methyl cytosine unchanged as a functioning cytosine, respectively.

The phrase "chemical conversion" as used herein, can refer to a molecule that is modified, altered or changed as a result of a reaction with a chemical that is capable of modifying, altering or otherwise changing the molecule. Cytosine being changed into uracil can be an example of a molecule (cytosine) subject to a chemical conversion when reacted with sodium bisulfite in which the chemical conversion comprises bisulfite conversion followed by an optional step of desulfonation.

The phrase "conversion reagent" as used herein, can refer to a reagent capable of modifying, altering or otherwise changing a molecule. For example, sodium bisulfite is a conversion reagent that can convert cytosine to uracil, optionally followed by desulfonation.

The phrase "conversion/purification" as used herein, can refer to a reaction involving a nucleic acid in which the nucleic acid undergoes a physical, chemical, structural or other change as would be known to one of skill in the art in which the nucleic acid has changed from the pre-conversion state or reaction. Following the conversion of the nucleic acid, for example, including but not limited to, a conversion with or without desulfonation, it is then sequentially purified from the components of the proceeding reaction such that the converted nucleic acid is isolated in a pure state, free of conversion reagents.

As used herein, "modification" as used herein, an refer to altering, modifying or otherwise changing a molecule's composition; physically, chemically and/or structurally or other change as would be known to one of skill in the art in which a nucleic acid has been changed from the pre-modification state or reaction. Modifications to the nucleic acid can include, but are not limited to, methylation, glycosylation, phosphorylation and acetylation.

The phrase "extraction reagent" as used herein, can refer to a reagent capable of removing or separating an entity, e.g., a nucleic acid, from its naturally occurring state to an isolated or purified state.

The term "isolated" as used herein, can refer to an entity or molecule, e.g. a protein, nucleic acid, a bead, and so on that is separate from e.g., other naturally occurring molecules, chemicals, chemical reagents and so on such that it can be considered substantially pure or purified.

The phrase, "sterile environment" as used herein can refer to an environment absent or free of detectable contamination, contaminants or materials otherwise foreign to the environment being described as sterile.

As used herein, the acronym "FFPE" as used herein denotes Formalin-Fixed, Paraffin Embedded. FFPE is a method used in preservation of a tissue sample in which the sample can be fixed in a formalin solution coupled with application of a wax referred to as paraffin.

As used herein, the term "kit" can refer to any system for delivering materials. In the context of nucleic acid-based isolation and structural or chemical conversions, such delivery systems can include elements allowing the storage, transport, or delivery of reaction components such as test samples, reagents, consumables such as collection, reaction, storage, microfuge and sample tubes, reaction reservoir tube/reaction vials, pipet tips, magnetic particles and the like in the appropriate containers from one location to another or to outfit a reaction platform when processing is within a single closed automated device, and commonly provided with written instructions for performing the methods for nucleic acid isolation and structural or chemical conversions. Kits can include one or more enclosures or boxes containing the relevant reaction reagents and supporting materials. The kit can comprise two or more separate containers wherein each of those containers includes a portion of the total kit components. The containers can be delivered to the intended recipient together or separately.

As used herein, "methylation" as used herein, can refer to substituting a group or atom with a methyl group or adding a methyl group to a substrate.

As used herein, "desulfonation" as used herein, can refer to the removal of sulfur (S) or $SO_3H$ on a nucleic acid.

The terms "nucleic acid," "polynucleotide," and "oligonucleotide" are used herein to include a polymeric form of nucleotides of any length, including, but not limited to, ribonucleotides and deoxyribonucleotides. Relatively short nucleic acid polymers are often used as "primers" or "probes". The definition encompasses nucleic acids from natural sources that can be methylated or capped, and also synthetic forms, which can contain substitute or derivatized nucleobases and may be based on a peptide backbone. Nucleic acids are generally polymers of adenosine, guanine, thymine, and cytosine and their "deoxy-" forms, but may also contain other pyrimidines such as uracil and xanthine, or spacers and universal bases such as deoxyinosine. Deoxynucleic acids may be single-stranded or double-stranded depending on the presence or absence of complementary sequences, and on conditions of pH, salt concentration, temperature, and the presence or absence of certain organic solvents such as formamide, n,n-dimethylformamide, dimethylsulfoxide, and n-methylpyrrolidinone.

As used herein, the term "cDNA" as used herein, can refer to complementary DNA. The DNA can be synthesized in a reaction catalyzed by the enzymes reverse transcriptase and DNA polymerase from a messenger RNA (mRNA) template.

As used herein, the phrase "genomic DNA" as used herein, can refer to chromosomal DNA, abbreviated as gDNA for genomic deoxyribonucleic acid. gDNA includes the genetic material of an organism.

The phrase "nucleic acid isolation" as used herein, can refer to the extraction of nucleic acid from the nucleus of a cell and removal of the nucleic acid from the non-nucleic acid nuclear and cellular debris including but not limited to extracellular milieu including environmental, tissue or organ matter and the like of a sample from which the nucleic acid was obtained.

As used herein the terms "magnetic particle", "bead", "nanoparticle", and "microsphere" as used herein, can refer to a magnetic microbead having at least one dimension, such as apparent diameter or circumference, in the micron or nanometer range. An upper range of such dimensions is 600 μm, but typically apparent diameter is under 2000 nm, and may be 1-50 μm or 50-1000 nm, while not limited to such. Such particles may be composed of, contain cores of, or contain granular domains of, a paramagnetic or superparamagnetic material, such as the $Fe_2O_3$ and $Fe_3O_4$ (α-Fe crystal type), α'-FeCo, ε-Cobalt, CoPt, $CrPt_3$, $SmCO_5$, Nickel and nickel alloys, $Cu_2MnAl$, α-FeZr, $Nd_2Fe_{14}B$, NoTi, for example. Ferrites, defined as ferrimagnetic or ceramic compound materials consisting of various mixtures of iron oxides such as Hematite ($Fe_2O_3$) or Magnetite ($Fe_3O_4$) and iron oxides in alloys with other metals are commonly used and known to one of skill in the art of nucleic acid isolation. These materials as used generally are particles having dimensions smaller than a magnetic domain, and may be formed into particles, beads or microspheres with binders such as latex polymers (generically), silica, as is generally well known and inclusive of such materials as are commercially available.

Nanoparticles of $Fe_3O_4$ with diameters in the 50 nm-100 μm range as are commercially available for magnetic bioseparations. These particles are "superparamagnetic", meaning that they are attracted to a magnetic field but retain no residual magnetism after the field is removed. Therefore, suspended superparamagnetic particles tagged to the biomaterial of interest can be removed from a matrix using a magnetic field, but they do not agglomerate (i.e., they stay suspended) after removal of the field. Also of interest are nickel and cobalt microbeads. These beads may be reactive with peptides containing histidine. Magnetic microbeads may be composite materials. Such beads may further contain other micro- or nanoparticles agglomerated with a binder. Composites with RF-tags, QDots, up-converting fluorophores, colloid sols and clays, and the like are contemplated for use in the present invention. A magnetic bead need not be formed entirely of a magnetic material, but may instead comprise both magnetic and non-magnetic materials.

Suitable microbeads for practicing the present invention may also be purchased from vendors such as Bang's Laboratories, Inc. (Fishers Ind.) and Polysciences, Inc (Warrington Pa.), as well as numerous suppliers of specialty modified microbeads such as Bioscience Beads (West Warwick R.I.). Trade names of such beads, again not as a comprehensive recitation, include Estapor® SuperParaMagnetic Microspheres, COMPEL™ Uniform Magnetic Microspheres, Dynabeads® MyOne™ Microspheres, and the like. Cobalt paramagnetic microbeads are sold as Dynabead's MyOne TALON. BioMag Plus microbeads from Polysciences have an irregular shape, and thus more surface area for affinity chemistry.

The phrase "over layer with mineral oil" as used herein, can refer to the application of mineral oil to the top of a reaction, e.g., a PCR reaction, or on top of a reagent, e.g., sodium bisulfite reagent, to preclude exposure to air, prevent evaporation upon heating, avoid oxidation, and so on. The mineral oil would be understood by one of skill in the art to be air-impermeable, non-reactive with the reaction or reagent it was in contact with and thus inert.

"PCR" is an abbreviation of term "polymerase chain reaction," the nucleic acids amplification technology used in all methods of the present invention, and which was originally discovered and described by Mullis K. B. et al, U.S. Pat. No. 4,683,195 and Mullis K. B., U.S. Pat. No. 4,683, 202. In some embodiments, PCR employs two oligonucleotide primers for each strand that are designed such as extension of one primer provides a template for another primer in the next PCR cycle. Either one of a pair of oligonucleotide primers can be named herein as a "forward" or "reverse" primer with the purpose of distinguishing the oligonucleotide primers in discussion. A PCR can consist of repetition (or cycles) of (i) a denaturation step which separates the strands of a double stranded nucleic acid, followed by (ii) an annealing step, which allows primers to anneal to positions flanking a sequence of interest; and then (iii) an extension step which extends the primers in a 5' to 3' direction thereby forming a nucleic acid fragment complementary to the target sequence. Each of the above steps can be conducted at a different temperature using an automated thermocycler. The PCR cycles can be repeated as often as desired resulting in an exponential accumulation of a target DNA fragment whose termini are usually defined by the 5' ends of the primers used. Certain exceptions to this rule can apply, including those described herein. Particular temperatures, incubation time at each step and rates of change between steps depend on many factors well-known to those of ordinary skill in the Art and the examples can be found in numerous published protocols, for example, McPherson M. J. et al. (1991 and 1995) and the like. Although conditions of PCR can vary in a broad range, a double-stranded target nucleic acid can be denatured at temperature >90° C., primers can be annealed at a temperature in the range 50-75° C., and the extension can be performed in the range 72-78° C.

The phrase "quantitative PCR" or "qPCR" as used herein, can refer to a PCR designed to measure the abundance of one or more specific target sequences in a sample. Quantitative measurements can be made using one or more reference nucleic acid sequences that can be assayed separately or together with a target nucleic acid. Techniques for quantitative PCR are well known in the art and they are exemplified in the following manuscripts that are incorporated herein by reference: Gu Z. et al (2003) J. Clin. Microbiol., 41:4636-4641; Becker-Andre M. and Hahlbrock K. (1989) Nucleic Acids Res., 17:9437-9446; Freeman W. M. et al (1999) Biotechniques, 26:112-122, 124-125; Lutfalla G. and Uze G. (2006) Methods Enzymol., 410:386-400; Clementi M. et al (1993) PCR Methods Appl. 2:191-196; Diviacco S. et al (1992) Gene, 122:313-320.

As used herein "reagent" as used herein, can refer broadly to any chemical or biochemical agent used in a reaction, including enzymes. A reagent can include a single agent which itself can be monitored (e.g., a substance that is monitored as it is heated) or a mixture of two or more agents. A reagent may be living (e.g., a cell) or non-living. Exemplary reagents for isolation of a nucleic acid can include at least one of, but are not limited to, buffer, lysis buffer, salt, a bead, a protease, an enzyme; exemplary reagents for nucleic acid amplification reaction include, but are not limited to, buffer, metal ion (for example magnesium salt), chelator, polymerase, primer, template, nucleotide triphosphate, label, dye, nuclease inhibitor, and the like. Reagents for enzyme reactions include, for example, substrates, chromogens, cofactors, coupling enzymes, buffer, metal ions, inhibitors and activators. Not all reagents are reactants.

As used herein "reservoir" as used herein, can refer to a vial used within a single closed automated system. The reservoir is utilized within the closed device, including but not limited to, for example the AnaPrep devices, for extraction of nucleic acid from a test sample in an integrated method of nucleic acid isolation and structural or chemical conversion of the isolated nucleic acid. The reservoir vial can withstand heating to 100° C. and can have a shape configured for application of a magnetic field by a magnet in which the reservoir is configured to the contours of the magnet. A separate reservoir can be used for; i. isolation of nucleic acid from a sample, ii. conversion of the isolated nucleic acid sample and iii. extraction of the converted nucleic acid.

The terms, "sample" and "test sample", are used interchangeably and as used herein, can refer to any substance containing or presumed to contain a nucleic acid of interest, and thus includes a sample of nucleic acid, cells, organisms, tissue, fluids (e.g., spinal fluid or lymph fluids), organic fluid taken from a patient, and a sample including but not limited to whole blood, plasma, serum, buffy coat, urine, tears, stool, respiratory and genitourinary tract swabs, saliva, cheek swab, sputum, cerebral spinal fluid, a formalin fixed paraffin embedded (FFPE) sample, fragments of different organs, a cell, a tissue, blood cells, circulating tumor cell (CTC) or a disseminated tumor cell (CTD), bone, samples of in vitro cell cultures or specimens that have been suspected to contain nucleic acid molecules.

Reference will now be made in detail to exemplary embodiments of the disclosed invention. While the disclosed methods and compositions will be described in conjunction with the exemplary embodiments, it will be understood that these exemplary embodiments are not intended to limit the disclosed invention. On the contrary, the disclosed invention is intended to encompass alternatives, modifications and equivalents, which can be included in the spirit and scope of the disclosed invention.

In some embodiments, disclosed is a method for performing automated sequential nucleic acid isolation(s) and conversion/purification reaction(s) in an integrated, single closed system. The isolated and converted nucleic acid is further used for modification and modification detection. In some embodiments, the modification includes, but is not limited to, a methylation, glycosylation, phosphorylation and acetylation reaction by means known to one of skill in the art to modify a nucleic acid. The modified nucleic acid is subsequently detected by means known to one of skill in the art, including but not limited to PCR, qPCR, sequencing, NGS, and so one. In some embodiments, the single closed automated system is built in a device. Integrating reagents within an automated instrument a complete system is achieved for sample preparation and nucleic acid conversion. The integrated process can prevent contamination and cross contamination of reagents and samples and can provide a sterile environment as the process occurs within a closed system. The reagents used for extraction and conversion are aliquoted into individual compartments of a cartridge at necessary reaction volumes, reagent cost savings is realized as only the amount of reagent needed for each sample's extraction and reaction are used preventing reagent waste and preserving sensitive reagents. Improvements in protecting sensitive reagents and preventing reagent evaporation have been made by overlaying mineral oil atop sensitive reagents or reagents subject to evaporation by heating. The process also provides controlled drying of nucleic acid:bead complexes formed during the extraction and conversion processes to both shorten extraction and reaction times but ensure consistent nucleic acid recoveries and thereby shorting total processing time compared to manual processes.

Extraction of nucleic acid for analysis of disease, PCR, DNA sequencing and other molecular biology processes can be a delicate, contamination vulnerable and tedious process. Automation processes for nucleic acid extraction are available from manufacturers such as Qiagen, Tecan, Hamilton, Thermo/Fisher, and Stratec (Invitec). However, each system is limited to nucleic acid extraction and does not integrate nucleic acid conversion reactions, thus requiring additional processing time, manual intervention and further opportunities for contamination of the often limited test sample. The Tecan and Hamilton systems are also open to the environment making reagent evaporation, contamination and cross-contamination, potentially by aspiration of fluids during transfer steps, an ongoing concern for researchers. The system from Stratec (Invitec) is a two-step system but the samples are uploaded external to the system and again fails to ensure protection from environmental or reagent contamination.

The disclosed invention solves the problem of contamination by integrating nucleic acid extraction and conversion reactions into a single, closed automated process. The nucleic acid-containing test sample is placed in a reaction tube then inserted into instrument. A suitable instrument has been developed, the AnaPrep device from BioChain® (BioChain Institute, Inc., Newark, Calif.) in which the nucleic acid is isolated within a closed system to prevent contamination. Following reacting the nucleic acid-containing sample with an extraction reagent, the isolated nucleic acid is obtained from the sample. The subsequent reaction of the isolated nucleic acid, within the AnaPrep, with a conversion reagent provides an integrated and automated process.

The reaction of isolated nucleic acid in a conversion reaction can further structurally or chemically convert the nucleic acid for further analysis or processes. One process can be restriction enzyme digest. Restriction enzymes, available from numerous suppliers, e.g. New England Biolabs, cut nucleic acid at specific positions resulting in altering the structure of the nucleic acid. The cuts can be blunt, or with 5' or 3' overhangs. Digesting nucleic acid can be used prior to a ligation reaction in which e.g., an adaptor is attached by a ligase to the digested nucleic acid. Such reactions are common in nucleic acid sequencing such as next generation methodologies well known to one of skill in the art.

In some embodiments, the conversion is a chemical conversion. In some embodiments, the chemical conversion is a bisulfite conversion, wherein the bisulfite conversion reagents have an over-layer of mineral oil. In some embodiments, the bisulfite conversion is deamination of cytosine into uracil, wherein 5-methylcytosine is not converted. In some embodiments, the bisulfite conversion comprises an optional step of desulfonation. In some embodiments, the isolation and conversion/purification of the nucleic acid occurs in less than about three and half hours and utilizes magnetic beads.

In some embodiments, disclosed is a method for performing sequential nucleic acid isolation integrated with a bisulfite conversion reaction in a single closed automated system comprising: introducing a nucleic acid-containing sample into a reaction tube, wherein said reaction tube is within a device for performing sequential nucleic acid isolation and conversion/purification in a single closed system; reacting the nucleic acid-containing sample with an extraction reagent; binding the extracted nucleic acid to magnetic beads subsequently added after the extraction reaction, wherein an isolated nucleic acid is obtained from the sample; reacting said isolated nucleic acid with a bisulfite conversion reagent, wherein the bisulfite conversion reagent has an over-layer of mineral oil; and binding the bisulfite-converted nucleic acid to magnetic beads subsequently added after the conversion reaction, wherein bisulfite-converted nucleic acid is obtained.

In yet another embodiment, the present invention provides the reduction of volume of the sample processing in a closed system, from section (A) comprises the nucleic acid isolation/extraction chamber to the other section (B) comprises the conversion/purification reaction chamber. Samples from section A with large volume are passed to section B becoming a smaller volume. In some embodiments, section A's sample volume ranges 1 ml, 2 ml, 3 ml, 4 ml, 5 ml, 6 ml, 7 ml, 8 ml, 9 ml, 10 ml, 15 ml and 20 ml. Particularly, the volume is ranging 1 ml to 4 ml. In one embodiment, volume in Section B with samples in the chamber is reduced to the ranges from 500 ul, 400 ul, 300 ul, 200 ul, 100 ul, 90 ul, 80 ul, 70 ul, 60 ul, 50 ul, 40 ul 30 ul, 20 ul, 10 ul, to 5 ul. Particularly, the volume is ranging 50 ul to 250 ul.

In some embodiments, disclosed is a method for nucleic acid extraction combined with bisulfite conversion comprising: a) contacting a sample with a first magnetic particle under conditions permissive for nucleic acid binding to said particle on an automated reaction platform, wherein DNA is bound to the first magnetic particle forming a first nucleic acid:particle complex; b) eluting the nucleic acid from the particle; c) contacting the eluted nucleic acid with a bisulfite reagent overlaid with mineral oil under conditions permissive for a bisulfite reaction to produce a converted nucleic acid within the nucleic acid with or without desulfonation; and d) eluting the bisulfite treated nucleic acid from a second magnetic particle in a second eluting step.

In some embodiments, disclosed is a method for performing sequential nucleic acid sample reaction(s) comprising: a) introducing a nucleic acid-containing sample into a reaction reservoir of a device for performing automated sequential nucleic acid isolation and conversion/purification in a single closed system via a pipet tip attached to the uni-directional auto sample head within said device; b) reacting the nucleic acid-containing sample with one or more reagents, wherein each reagent is transferred from its own compartment within a disposable cartridge within said device by separate pipet tips attached to the uni-directional auto sample head; c) separating the reacted nucleic acid from the reaction components; and d) eluting the reacted nucleic acid from a nucleic acid:particle complex in the reaction reservoir. In some embodiments, the particle within the nucleic acid: particle complex is selected from the group consisting of a magnetic particle, a magnetic bead, and a coated bead with a magnetic center. In some embodiments, the reaction reservoir is in contact with a magnet within the device, wherein the reaction reservoir is configured to the magnet. In some embodiments, steps a., b., c., and d. are repeated in succession for each sequential nucleic acid reaction, wherein a subsequent nucleic acid reaction is reacted in a second, a third, a fourth, etc. reaction reservoir within said device.

In some embodiments, the sample having the nucleic acid is combined with a lysis binding buffer, wherein the lysis buffer is extracted from a sealed chamber positioned within a reaction platform and wherein said sample and lysis buffer are combined in a first reaction reservoir on said reaction platform at a temperature of about 40° C. for about 360 seconds.

In some embodiments, prior to elution the extracted nucleic acid:particle complex is washed with a wash solution followed by drying the complex. In some embodiments, the nucleic acid is eluted from the particle by the addition of about 100 μl elution buffer and heated to 80° C.+/−2° C. with aspiration-blow action by the transfer tip for about 10 minutes. In some embodiments, the eluted nucleic acid is transferred from the first reaction reservoir to a second reaction reservoir where contact with the bisulfite reagent includes an over layer of mineral oil on top of the bisulfite reagent and the bisulfite reaction is performed at 80° C.+/−2° C. with for about 45 min.

In some embodiments, prior to elution the bisulfite converted nucleic acid:particle complex is washed with a wash solution followed by drying the complex. In some embodiments, about 1000 μl wash solution is mixed with the bisulfite treated nucleic acid and the second magnetic particle, wherein DNA is bound to the second magnetic particle forming a second nucleic acid:particle complex and the complex is mixed by aspirating/blowing action for about 250 times within the third reaction reservoir to bind converted nucleic acid to the particle and the washing may be repeated at least once. In some embodiments, the nucleic acid is eluted from the particle by the addition of about 60 μl elution buffer and heated to 23° C.+/−2° C. with aspiration-blow action for 250 times in by the transfer pipet tip in about 10 minutes.

Containing the reagents and magnetic particles, each within its own sealed compartment within the cartridge prevents contamination of the reagents as well as cross-contamination, allows aliquoting the required amount for each individual extraction and conversion reaction step and has provided an over layer of mineral to prevent evaporation of reagents subject to heating prior to use and protects reagents susceptible to oxidation or degradation upon exposure to air. Additionally, the reaction platform provides a single closed system within which automated nucleic acid extraction is integrated with a bisulfite conversion reaction of the extracted nucleic acid.

Figure 1:
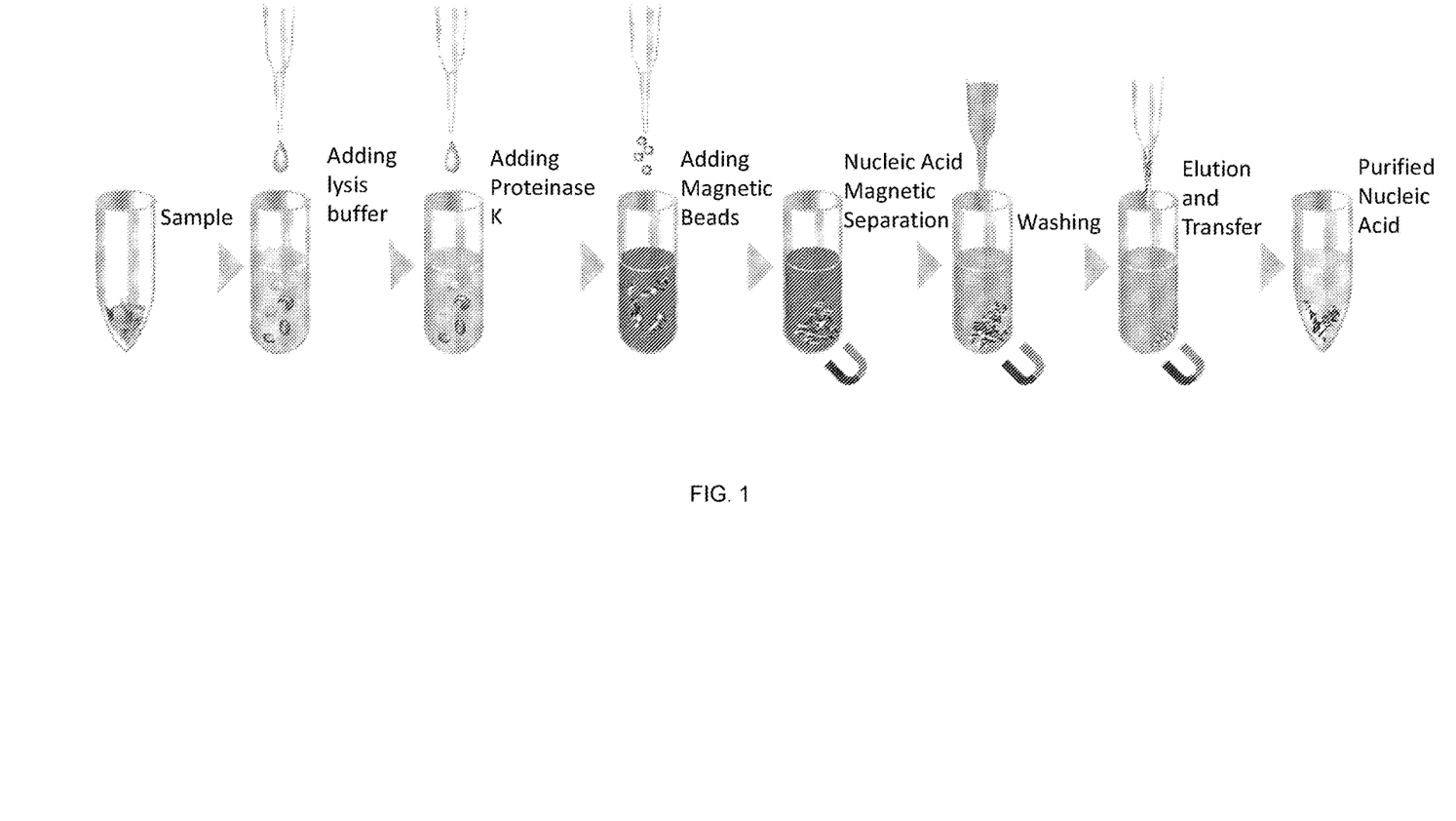
FIG. 1 illustrates a schematic for isolation of nucleic acid from a test sample, in accordance with various embodiments.
Figure 2:
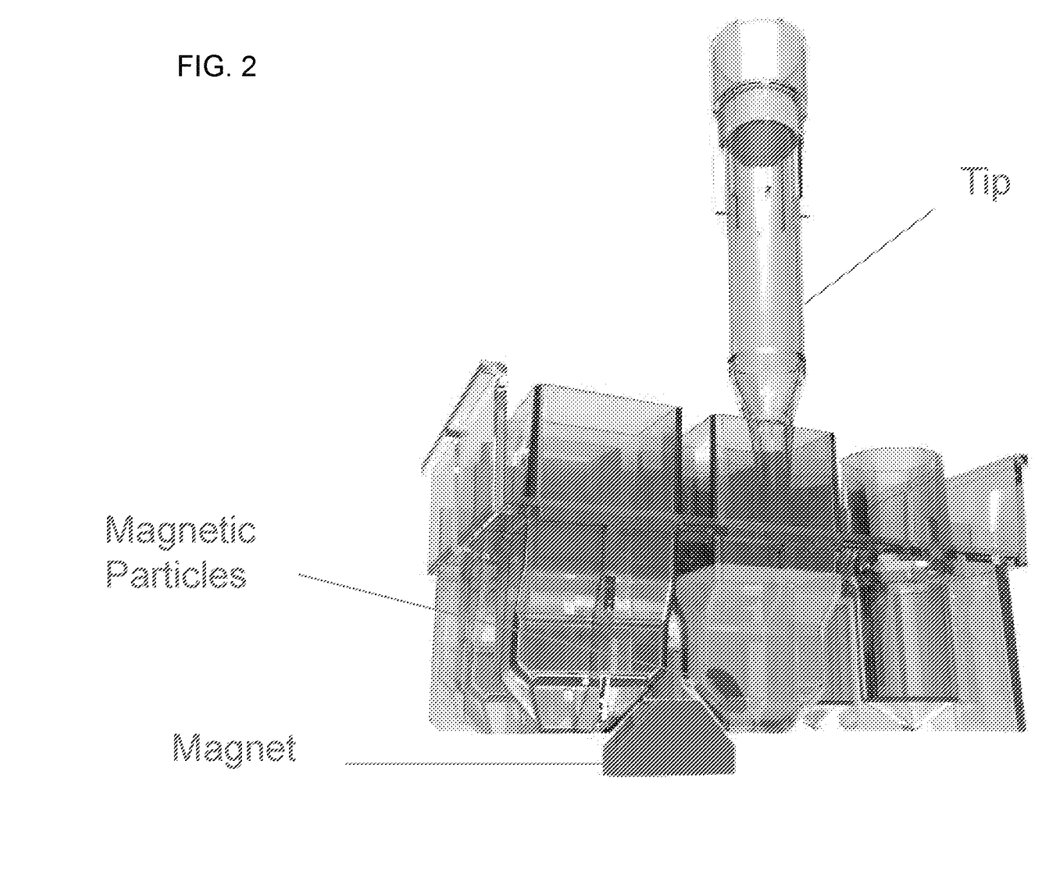
FIG. 2 illustrates a reaction reservoir configured to a magnet for extracting eluted nucleic acid from magnetic particles, in accordance with various embodiments.

In some embodiments, the reaction reservoirs used within the single closed automated device are configured to a magnet within the device. The magnet provides a magnetic attraction for the magnetic particle to the magnet. FIG. 2 illustrates the reaction reservoirs, magnet and pipet tip used to perform the integrated extraction and conversion or chemical reaction on the sample DNA within the disclosed device. The sequestering and separation the magnetic particle from the eluted nucleic acid and from the conversion reaction or chemically reacted nucleic acid after the nucleic acid is eluted from the nucleic acid:particle complex permits extraction of the eluent that is free of particles.

In a bisulfite conversion reaction, isolated nucleic acid can be reacted with a bisulfite reagent. Sodium bisulfite can be used to convert cytosine, but not 5-methyl cytosine, to uracil. The result is the introduction of targeted changes in the DNA sequence as a result of the DNA sequence's methylation status at each cytosine. Once the bisulfite-converted, followed by optional step of desulfonation, nucleic acid is prepared for modification detection, wherein the modification can be methylation. The nucleic acid is sequenced or amplified by PCR and analyzed information is obtained to detect each individual cytosine's methylation status.

Methylated DNA occurs naturally in prokaryotes and eukaryotes. In humans, methylated DNA has been implicated in epigenetics, genomic imprinting, embryonic development, X-chromosome inactivation and carcinogenesis. Human cytosines present in the CpG dinucleotide: 5'-CpG-3' (cytosines preceding guanines), are methylated by DNA methyltransferases, although non-CpG methylation patterns have also been found. Determining the DNA methylation status was made possible by discovering that bisulfite has a higher specificity for cytosine than 5-methylcytosine. Following conversion the DNA having undergone bisulfite conversion can be single stranded and non-complementary to its previously complementary strand as illustrated below:

|  | DNA Before Bisulfite Conversion | DNA After Bisulfite Conversion |
|---|---|---|
| Forward Strand | 5'TGCGCAAGCGCATGCCGCT (SEQ ID NO: 1) | 5'TGCGUAAGCGUATGUCGUT (SEQ ID NO: 2) |
| Reverse Strand | 3'ACGCGTTCGCGTACGGCGA (SEQ ID NO: 3) | 3'AUGCGTTUGCGTAUGGCGA (SEQ ID NO: 4) |

Methylated cytosine is indicated as "C" and non-methylated cytosine is indicated as "C". Methylated cytosines remain unchanged after bisulfite conversion but non-methylated cytosines have been converted to uracil indicated as "U". The converted nucleic acid strands are now non-complementary as uracil (U) does not pair with guanine (G).

Commercially available kits for manual sample preparation of methylated nucleic acids in reagent kits format are available from Qiagen, Zymo Research and BioChain. The Qiagen kit is marketed as the EpiTect Fast Bisulfite Conversion Kit. The Zymo Research kit is marketed as the EZ DNA Methylation™ Kit. BioChain markets DNA Methylation Detection Kits. Another commercially available kit for determination of methylated DNA for detection of colon cancer is the Epi proColon 2.0 CE (EpiGenetics, Berlin, Germany). It is also a manual, qualitative assay for the real-time PCR detection of methylated Septin9 DNA in bisulfite converted DNA from human plasma samples. Presence of methylated Septin9 is associated with, and may aid in, the detection of colorectal cancer. Epi proColon 2.0 CE is comprised of the Epi proColon Plasma Quick Kit (M5-02-001), the Epi proColon Sensitive PCR Kit (M5-02-002) and the Epi proColon Control Kit (M5-02-003).

The Epi proColon 2.0 CE utilizes PCR in an in vitro assay for the qualitative detection of Septin9 gene methylation in DNA isolated from 3.5 ml of patient plasma. It has been found that cytosine residues in the v2 region of the Septin9 gene become methylated in colorectal cancer (CRC) tissue but not in normal colon mucosa. The kit uses a patient blood sample for detection of Septin9 gene methylation status offering a reasonable alternative to screening colonoscopy for CRC screening. Detection of CRC DNA in plasma using the Septin9 methylation biomarker has been demonstrated in multiple case control studies of CRC patients and colonoscopy-verified negative controls.

The Epi proColon 2.0 CE involves two manual steps. In the first step DNA is extracted from plasma followed by bisulfite conversion of the purified DNA using the Epi proColon Plasma Quick Kit (M5-02-001). The bisulfite converted DNA (bisDNA) is assayed in a duplex PCR using the Epi proColon Sensitive PCR Kit (M5-02-002) which detects both the target methylated Septin9 DNA and an internal control, ACTB (8-actin) DNA, (Epi proColon Control Kit (M5-02-003)). The controls provide positive and negative controls for each run and to assess adequacy of the input DNA.

The extraction of DNA contained in patient plasma is based on the binding of free-circulating DNA to magnetic particles, which are then magnetically separated from the plasma. Remaining non-DNA impurities are removed from the magnetic particles by washing the DNA:particle complex. The DNA is eluted from the magnetic particles by dissolving the DNA in elution buffer. The eluate containing DNA is then treated in a bisulfite chemical reaction that specifically alters unmethylated cytosine residues within the DNA.

Blockers and probes are used in the subsequent PCR reaction to discriminate between methylated and unmethylated sequences. Epi proColon 2.0 CE detects a bisDNA sequence containing methylated CpG sites within the v2 region of the Septin9 gene and total bisDNA of a region of the ACTB gene. The Septin9 portion of the duplex assay consists of primers that are placed in regions lacking CpG dinucleotides. A blocker specific for bisulfite converted unmethylated sequences within the region is added so that methylated sequences are preferentially amplified. A methylated Septin9-specific fluorescent detection probe is used in the reaction in order to exclusively identify methylated sequences amplified during the PCR reaction.

In some embodiments, the sample is selected from the group consisting of whole blood, plasma, serum, buffy coat, urine, tears, stool, respiratory and genitourinary tract swabs, saliva, cheek swab, sputum, cerebral spinal fluid, a formalin fixed paraffin embedded (FFPE) sample, fragments of different organs, a cell, a tissue, blood cells, circulating tumor cell (CTC) or a disseminated tumor cell (CTD), bone, samples of in vitro cell cultures or specimens that have been suspected to contain nucleic acid molecules.

Figure 3A:
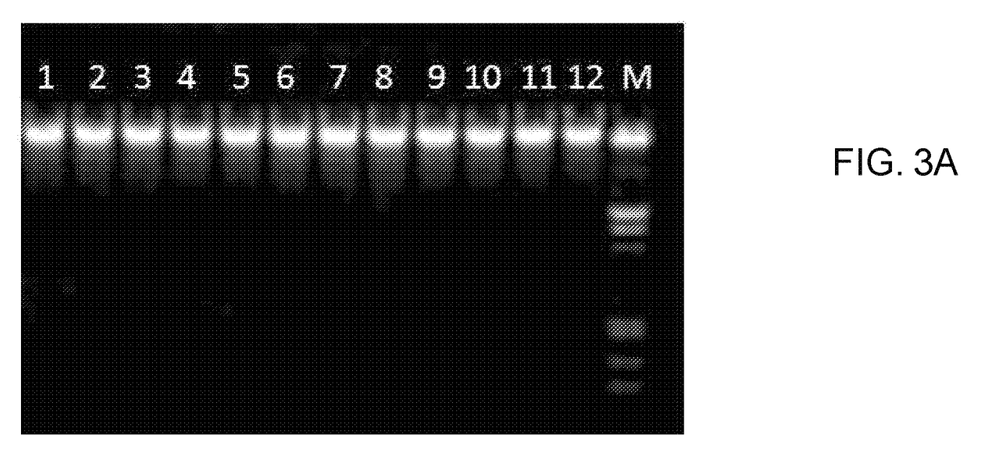
FIG. 3A is photograph of an agarose gel of genomic DNA extracted from human whole blood from 12 donors.

In some embodiments, the extracted nucleic acid is DNA, RNA, cDNA or a combination thereof. The disclosed methods have been shown to efficiently and reproducibly extract nucleic acids from a variety of sample types. FIG. 3A illustrates an agarose gel of 12 donors' genomic DNA extracted from human whole blood samples using the methods disclosed herein. The extracted gDNA appears unfragmented, of uniform concentration and free of contaminants that could interfere in downstream methods.

Figure 3B:
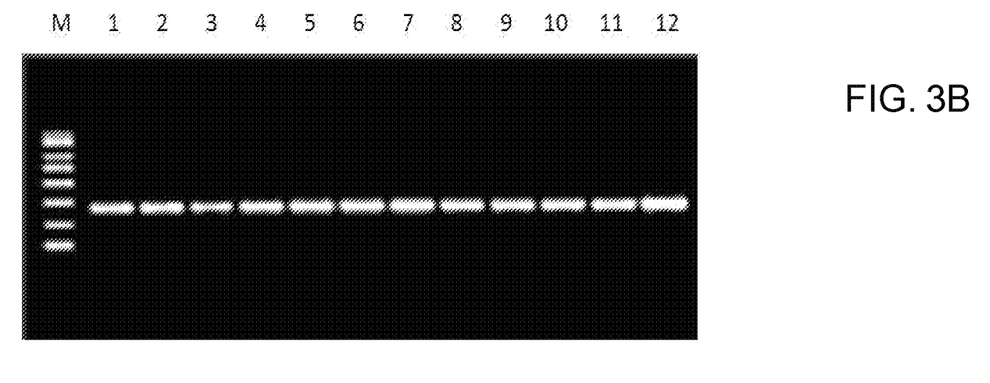
FIG. 3B is a photograph of an agarose gel of PCR products from the 12 donors' DNA used in PCR reactions, in accordance with various embodiments.

In some embodiments, the isolated nucleic acid is further suitable for PCR, qPCR, sequencing, restriction enzyme digestion, ligation, transfection, hybridization, genotyping, forensics testing, quality control, bisulfite reaction, methylation reaction, disease detection, prognosis, and molecular diagnosis. In some embodiments, the isolated nucleic acid can be reacted in a sequential nucleic acid reactions selected from the group consisting of an enzymatic, extension, hybridization, ligation, polyadenylation, deamination, methylation or blotting as is known to one of skill in the art. FIG. 3B depicts an agarose gel electrophoresis of the same 12 donors' gDNA from FIG. 3A used in a qPCR reaction. The resulting PCR products are each of high consistency and reproducibility between the 12 extracted gDNAs.

Figure 4A:
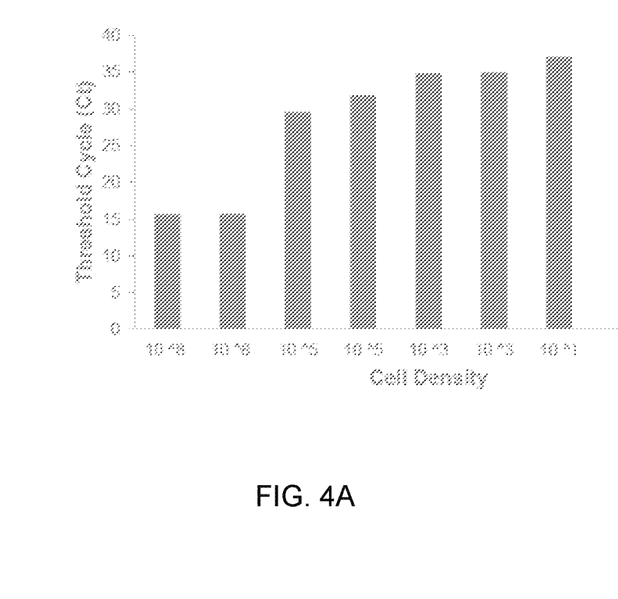
FIG. 4A graphically illustrates the scalability of the DNA extraction method disclosed and FIG. 4B the reaction order of the extraction reactions in FIG. 4A, as evidence the disclosed method has no cross contamination.
Figure 4B:
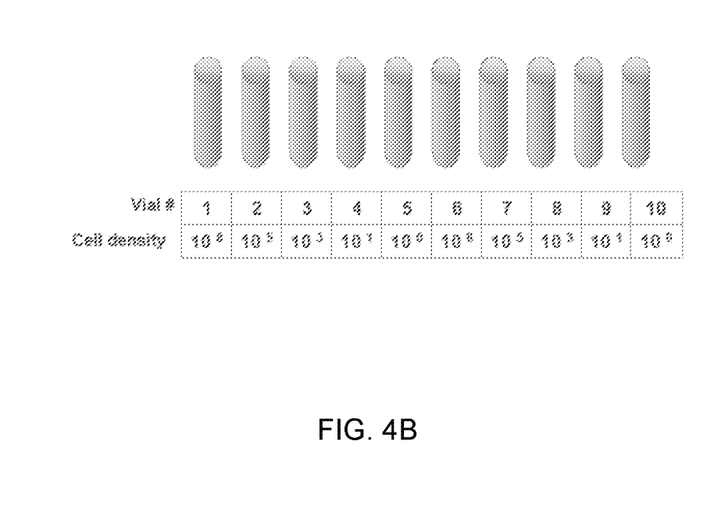

FIG. 4A is a graphical representation of blood plasma spiked with E. coli cells at four different cell densities. The E. coli nucleic acid was extracted from the blood plasma using the disclosed methods followed by qPCR analysis. The graft demonstrates that the disclosed methods are scalable irrespective of the DNA concentration within the test sample. FIG. 4B illustrates the order processing of the E. coli spiked blood plasma samples and when viewed together with FIG. 4A further demonstrates that the disclosed method is free of cross-contamination when processed in a single closed automated system such as the disclosed device.

Figure 5A:
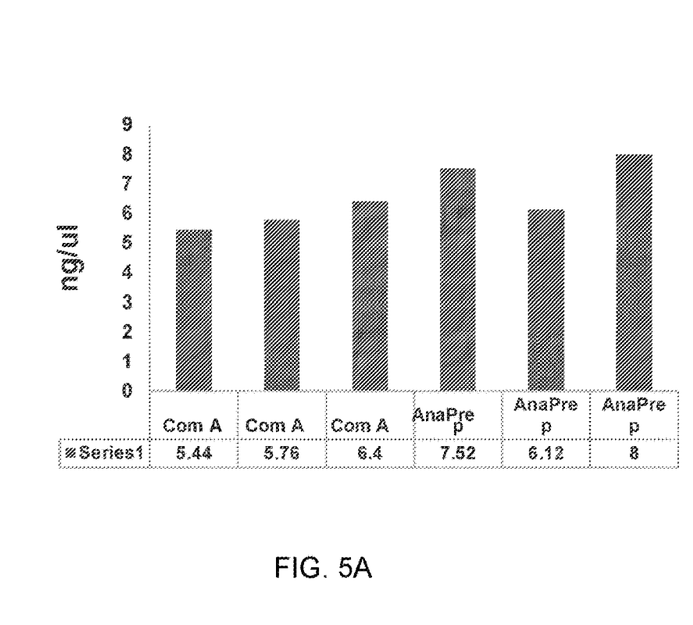
FIG. 5A graphically illustrates a comparison of the disclosed method and that of a commercial product offering used to extract DNA from the same block of FFPE pancreas tissue and FIG. 5B provides another comparison of the two methods using the extracted DNA in a qPCR reaction using β-actin as the target.
Figure 5B:
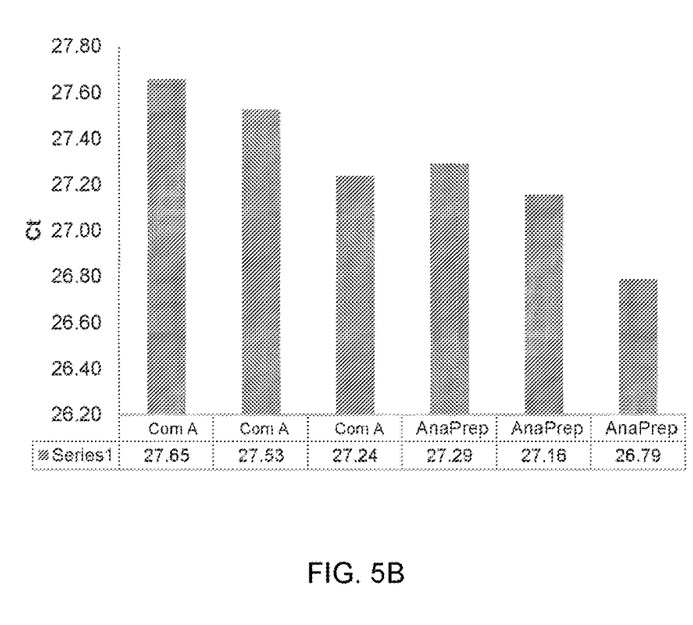
Figure 6A:
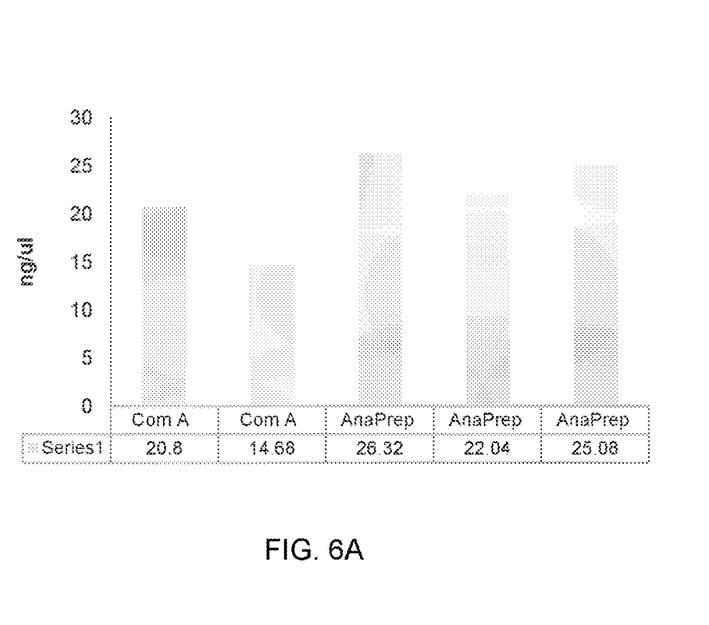
FIG. 6A graphically illustrates a comparison of the disclosed method and that of a commercial product offering used to extract DNA from the same block of FFPE spleen tissue and FIG. 6B provides another comparison of the two methods using extracted DNA in a qPCR reaction using β-actin as the target.
Figure 6B:
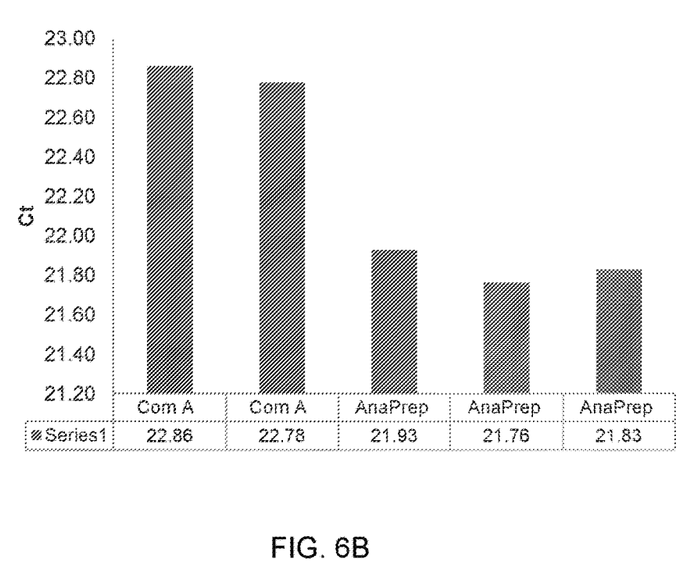

Processing of FFPE samples to recover nucleic acid, e.g., DNA, is a known to be a difficult and often frustrating process because of chemicals used in the FFPE process are known to degrade the desired DNA and the amount of DNA recovered is notoriously low. As depicted in FIG. 5A, DNA was extracted in six separate extraction reaction from FFPE slides from the same human pancreas tissue block. The extraction reactions were done in triplicate testing two different instrumentation systems. The disclosed automated extraction method and device consistently resulted in greater DNA recovery when compared to another device system. Further, as illustrated in FIG. 5B, the resulting extracted DNA from the disclosed integrated method and device system had better qPCR results using f3-actin as the target. Similar comparisons were also tested with spleen DNA extracted from five FFPE slides from the same human spleen tissue block. FIG. 6A illustrates the greater overall recover of extracted DNA using the disclosed integrated method and device and FIG. 6B illustrates that qPCR analysis of the extracted DNA had better results using f3-actin as the target. The disclosed methods for nucleic extraction integrated with nucleic acid conversion conducted within the disclosed single closed automated device deliver consistent, replicable, scalable, nucleic acid recovery and at a greater yield of nucleic acid and downstream conversion of the nucleic acid provides consistent, actionable data suitable for various application for genetic sample analysis, including but not limited to, epigenetic analysis, DNA sequencing, methylation-sensitive single-strand conformation analysis (MS-SSCA), High Resolution Melting analysis (HRM), Methylation-Sensitive Single-nucleotide Primer Extension (MS-SnuPE), Base-specific cleavage/MALDI-TOF, Methylation-specific PCR (MSP) and Microarray-based methods as are known to one of skill in the art.

In some embodiments, disclosed is a device for performing automated sequential nucleic acid isolation and conversion/purification in a single closed automated system comprising: reaction tubes for processing and reacting a test sample; at least one disposable, at least one sealed cartridge containing a plurality of sealed compartments containing reagents, wherein reagents have an over-layer of mineral oil, wherein said reagents are used in extraction and conversion/purification of nucleic acids from the test sample; a heating unit capable of contacting a plurality of reaction tubes, wherein each reaction tube contains at least one of the extraction reaction and the conversion reaction and a magnet configured to the reaction tubes. In some embodiments, the device further has a UV lamp, a uni-directional auto sample head, wherein said sample head is synchronized with a stage moving within said device, automated liquid handling, a plurality of reaction reservoirs and a heat block. In some embodiments, the single closed device is an automated system, is sealed from the external environment such as a closed compartment and can be a sterile environment. In some embodiments, the isolation and conversion/purification of the nucleic acid occurs in less than about three and half hours wherein the isolation and conversion/purification of the nucleic acid is a bisulfite conversion. In some embodiments, the reaction is methylation, wherein cytosine is converted into 5-methyl cytosine. In some embodiments, the bisulfite conversion is deamination of cytosine into uracil, wherein 5-methylcytosine is not converted. In some embodiments, a bisulfite conversion comprises an optional step of desulfonation. In some embodiment, a modification comprises methylation. The present invention provides the reduction of volume of the sample processing in such device, from section (A) comprises the nucleic acid isolation/extraction chamber to the other section (B) comprises the conversion/purification reaction chamber. Samples from section A with large volume are passed to section B becoming a smaller volume. In some embodiments, section A's sample volume ranges 1 ml, 2 ml, 3 ml, 4 ml, 5 ml, 6 ml, 7 ml, 8 ml, 9 ml, 10 ml, 15 ml and 20 ml. Particularly, the volume is 2 to 4 ml. In one embodiment, volume in Section B with samples in the chamber is reduced to the ranges from 500 ul, 400 ul, 300 ul, 200 ul, 100 ul, 90 ul, 80 ul, 70 ul, 60 ul, 50 ul, 40 ul 30 ul, 20 ul, 10 ul, to 5 ul. Particularly, the volume is 5 to 50 ul.

In some embodiments, disclosed is a kit for performing sequential nucleic acid isolation and conversion/purification reaction(s) in a single closed system having: a plurality of reaction tubes, wherein said tubes are utilized on an automated platform; an extraction reagent that isolates nucleic acid from the nucleic acid-containing sample in a first reaction tube; a bisulfite reagent that converts unmethylated cytosine in the isolated nucleic acid to in a second reaction tube to produce a converted nucleic acid, wherein said bisulfite reagent further comprises an overlay of mineral oil; a plurality of magnetic particles, wherein said particles form a nucleic acid:particle complex with nucleic acid isolated in an extraction reaction in said first reaction tube, and wherein a separate aliquot of magnetic particles forms a nucleic acid:particle complex with bisulfite converted nucleic acid in said second reaction tube.

Any of the methods and reagents used to performing sequential nucleic acid isolation and conversion/purification reaction(s) in a single closed system as described herein can be included in a kit. In a non-limiting example the kit, in suitable container means, can have: a plurality of reaction tubes, wherein said tubes are utilized on an automated platform; an extraction reagent that isolates nucleic acid from the nucleic acid-containing sample in a first reaction tube; a bisulfite reagent that converts unmethylated cytosine in the isolated nucleic acid to in a second reaction tube to produce a converted nucleic acid with or without desulfonation, wherein said bisulfite reagent further comprises an overlay of mineral oil; a plurality of magnetic particles, wherein a first aliquot of said particles form a nucleic acid:particle complex with nucleic acid isolated in an extraction reaction in said first reaction tube, and wherein a second aliquot of magnetic particles forms a nucleic acid:particle complex with bisulfite converted nucleic acid in said second reaction tube. The kit can further contain adapters, primers and/or reagents useful for ligation, sequencing, restriction enzyme digestion, ligation, transfection, hybridization, genotyping, forensics testing, quality control, bisulfite reaction, methylation reaction, disease detection, prognosis, and molecular diagnosis. The kit can further optionally contain a DNA-polymerase. The kit can further optionally contain reagents for amplification, for example reagents useful for PCR amplification and qPCR methods. The kit can further optionally contain reagents for sequencing, for example, reagents useful for next-generation massively parallel sequencing methods.

The containers of the kits can include at least one vial, tube, test tube, sealed cartridge containing reagents or other containers, into which a reaction reagent can be placed, and preferably, suitably aliquoted. Where there is more than one component in the kit, the kit also can contain a second, third or other additional containers or cartridges into which the additional reaction reagents can be separately placed. However, various combinations of components can be included in a container or cartridge.

When the reaction reagents of the kit can be provided in one or more liquid solutions, the liquid solution can be an aqueous solution. However, the reaction reagents of the kit can be provided as dried powder(s). The reaction reagents can also have an over layer of mineral oil to prevent reagent evaporation or degradation upon exposure to air. When reagents are provided as a dry powder, the powder can be reconstituted by the addition of a suitable solvent.

A kit can include instructions for employing the kit reaction reagents as well the use of any other reagent not included in the kit. Instructions can include variations that can be implemented.

WORKING EXAMPLES

This invention has adapted a manual sample preparation for converting nucleic acids into methylated nucleic acids within an automated sample preparation system for methylating nucleic acids. The manual method is currently available as a sample preparation part of a diagnostic kit for colorectal cancer offered by Epigenomics. An automated and a manual method for sample preparation for methylated nucleic acids were conducted side by side to illustrate the improvements in nucleic acid sample isolation integrated with bisulfite conversion of the isolated nucleic acid as described herein for the disclosed invention. Both methods obtained similar results indicating that the automated method for sample preparation for methylated nucleic acids can be an improved method to the manual method.

The comparison process included sample collection and handling. Both a manual method to prepare methylated nucleic acid from plasma and an automated system to prepare methylated nucleic acid from plasma, PCR setup, analysis with the Applied Biosystems 7500 Fast and 7500 Fast Dx PCR Instruments.

Sample Collection and Handling
1. Blood Collection and Blood Storage

Blood collection and blood storage was performed according to the following condition(s) and procedures: A Vacutainer® K2EDTA 10 ml tube or S-Monovette® 9 ml Potassium-EDTA was used for drawing blood following manufacturer's recommendations for performing the blood draw. Blood was either processed immediately or stored at 2 to 8° C. for up to 24 hours prior to plasma preparation. The blood sample cannot be allowed to freeze. Alternatively S-Monovette@ 8.5 ml CPDA tube can be used for drawing blood.

2. Plasma Sample Preparation and Plasma Storage

The brake was disabled from functioning in the centrifuge used to spin blood samples to prevent disruption of the cell layer. The blood in blood collection tube was spun in the centrifuge for 12 min at 1350±150 rcf. Conversion of revolutions per minute (rpm) to rcf, can be found by referring to the centrifuge user manual.

Following centrifugation the blood collection tube is removed from the centrifuge. Using a fresh 15 cm disposable transfer pipette the plasma layer is transferred from the collection tube to a 15 ml polypropylene centrifuge tube with conical bottom. The plasma is then centrifuged in the 15 ml centrifuge tube for 12 min at 1350±150 rcf.

Following centrifugation the plasma within the 15 ml centrifuge tube is extracted using a fresh extra-long (22.5 cm) disposable transfer pipette or serological pipette, transferring 3.5 ml plasma into a labeled cryovial or centrifuge tube. Plasma samples can be stored at −15 to −25° C. for up to 4 weeks. If using a Vacutainer® K2EDTA 10 ml tube, plasma sample may be stored at 2 to 8° C. for up to 18 hours.

Manual Method to Preare Methylated Nucleic Acid from Plasma

Plasma samples containing circulating DNA as well as blood components were prepared using manual methods and kits purchased from Epigenomics. The Epi proColon 2.0 CE kit has three separate kits: the Epi proColon Plasma Quick Kit (M5-02-001), the Epi proColon Sensitive PCR Kit (M5-02-002) and the Epi proColon Control Kit (M5-02-003). The Plasma Quick Kit was used according to manufacturer's directions.

EXAMPLES

I. Automated Sample preDaration System to preDare Methylated Nucleic Acid from Plasma The automated sample preparation system is performed on the AnaPrep device from BioChain. Reagent cartridges, reaction reservoirs, reaction, sample and converted nucleic acid tubes are additional consumables to be provided to the user.

A. Pre-fill reagent cartridges are available, built to order depending on the conversion reaction to be performed in an integrated manner following isolation of nucleic acid for a test sample.

Reagent Cartridge contents for isolation of nucleic acid from a sample are comparable in composition to the reagents within the AnaPrep Blood DNA Extraction Kit 200 or 1200 (BioChain, P/N Z1322001 or Z1322002, respectively), AnaPrep Bacterial DNA Extraction Kit (Z1322006), and AnaPrep FFPE DNA Extraction Kit (Z1322009) kits except as noted:

1. Ethanol
2. Tip Wash Buffer
3. Wash A Buffer
4. Magnetic Beads
5. Lysis buffer
6. Lysis buffer
7. Lysis buffer
8. Lysis buffer
9. Lysis buffer
10. Lysis buffer
11. Protection buffer (Covered with mineral oil)
12. Conversion (BiSulfite) solution (Covered with mineral oil)
13. Wash A buffer
14. Magnetic Beads
15. Wash B Buffer
16. Wash B buffer 17. Elution Buffer
18. Desulfonation Buffer (optional)
19. Tip Wash Buffer
20. Tip Wash Buffer A. Automated Instrument: Features and Components
1. Prepare 12 to 48 sample in parallel
2. 12 to 48 pistons connect to liquid tips to perform liquid handling
3. X-Y-Z robotic arm to move liquid from chambers to reaction reservoirs
4. Magnet strip at bottom of reaction reservoir 1 and 3 to separate magnetic beads from liquid
5. Heat blocks to heat up reaction reservoir 2 and reaction reservoir 1 up to 100° C. for conversion and elution.
6. Platform to hold reagent cartridge, Reaction reservoirs, Tip holder
7. Rack to hold samples Tubes and elution tubes
8. Central Processing Unit (CPU) or microprocessor with firmware to control mechanical or electronic events and actions.
9. Scanner to scan barcode for samples, reagents
10. Software with feature Regulatory compliance for diagnostic application B. Consumables for automated system
1. Tip holder to hold liquid tip and piercing pin
2. Liquid tip and piercing pin
3. Reaction reservoirs C. Process of automated Sample Preparation System for methylated Nucleic acid The automated sample preparation was conducted on the AnaPrep device from BioChain® (BioChain Institute, Inc., Newark, Calif.). The method included:

1. Loading sample in 8 ml tube containing 3.5 ml plasma on sample rack
2. Load 1.5 ml collection tube on sample rack
3. Load reagent cartridge, Tip holder with liquid tip and piercing pin, and reaction reservoir.
4. Turn on power. Instrument starts initiating. Press 0 at Select protocol interface. Input 8870 at Program Code interface. Press Enter to start program.

D. Automated Instrument Process
1. Increase temperature of heating block to 40° C.
2. Pick up piercing pin and pierce the first set of sealed covers on reagent cartridge. Remove piercing pin.
3. Pick up liquid tip and elevate magnet strip.
4. Mix beads in beads chamber with liquid tip and aspirate beads
5. Transfer beads to reaction reservoir 1, take supernatant and go back to beads chamber to rinse beads left in the chamber. Mixing beads left with liquid tip and aspirate beads and transfer beads to reaction reservoir 1 again. Apply magnet strip at one side-bottom of reaction reservoir 1 to attract beads and aspirate supernatant from another side-bottom of reaction reservoir 1.
6. Aspirate 1/6 plasma and transfer to number 1 lysis buffer chamber, aspirate-blow the plasma-lysis buffer mixture for 10 times. Repeat this step for 5 times from number 2 lysis buffer chamber to number 6 lysis buffer chamber
7. Lyse plasma for 360 seconds
8. Lower down magnet strip and transfer plasma-lysis buffer mixture from number 1 chamber to reaction reservoir 1 containing beads. Transfer ethanol from ethanol chamber and add to reaction reservoir 1. Mix the plasma-lysis buffer mixture with beads by aspirate-blow action for 50 times to bind nucleic acid to the beads. Elevate magnet strip to attract beads and remove supernatant. Repeat this step for 5 times from number 2 chamber to number 6 chamber containing plasma-lysis buffer mixture.
9. Lower down magnet strip. Transfer wash A buffer 1000 ul from wash A buffer chamber and add to reaction reservoir 1 to wash beads by aspirate-blow action. Elevate magnet strip to attract beads and remove supernatant.
10. Dry bead in reaction reservoir 1.
11. Wash liquid tip three times with Tip Wash buffer to remove residue ethanol and salt carried from wash A buffer.
12. Lower down magnet strip. Increase the temperature of heating block to 80±2° C. Transfer 100 ul of elution buffer from elution buffer chamber and add to reaction reservoir 1 to elute nucleic acid by aspirate-blow action for 60 times in 10 minute. Elevate magnet strip to attract beads and transfer eluted nucleic acid in supernatant (eluent) to protection solution chamber with 25 ul of protection solution. Keep the temperature of heating block at 80±2° C.
13. Mix nucleic acid eluent with protection solution and transfer eluent and protection solution mixture to conversion solution chamber with 125 ul of conversion solution. Mix mixture containing nucleic acid eluent, protection solution, and conversion solution. Transfer the all mixture (about 250 ul) with mineral oil to reaction reservoir 2 and heat at 80±2° C. for 45 minutes. Remove liquid tip.
14. Pick up piercing pin and pierce the second set of sealed covers on reagent cartridge. Remove piercing pin.
15. Pick up a fresh liquid tip and elevate magnet strip.
16. Mix beads in beads chamber in reagent cartridge with liquid tip and aspirate beads
17. Transfer beads to reaction reservoir 3, take supernatant and go back to beads chamber to rinse beads left in the chamber. Mixing beads left with liquid tip, aspirate beads, and transfer beads to reaction reservoir 3 again. Apply magnet at one side-bottom of reaction reservoir 3 to attract beads and aspirate supernatant from another side-bottom of reaction reservoir 3.
18. Lower down magnet strip and transfer the 250 ul of mixture containing nucleic acid eluent, protection solution, and conversion solution from reaction reservoir 2 to reaction reservoir 3 containing beads. Transfer 1000 ul of wash A buffer to reaction reservoir 3 and mix by aspirate/blow action for 250 times to bind converted nucleic acid to beads.
19. Elevate magnet strip to attract beads in reaction reservoir 3 and remove supernatant twice.
20. Wash liquid tip 3 times with Tip wash buffer.
21. Transfer 800 ul of wash A buffer from wash A buffer chamber and add to reaction reservoir 3, and optionally adding 100 ul of desulfonation buffer, to wash beads by aspirate-blow action. Elevate magnet strip to attract beads and remove supernatant.
22. Transfer 800 ul of wash B buffer from wash B buffer chamber and add to reaction reservoir 3 to wash beads by aspirate-blow action. Elevate magnet strip to attract beads and remove supernatant.
23. Transfer 400 ul of wash B buffer again from wash B buffer chamber and add to reaction reservoir 3 to wash beads by aspirate-blow action. Elevate magnet strip to attract beads and remove supernatant.
24. Wash liquid tip 6 times with Tip wash buffer 25. Dry beads with liquid tip inside reaction reservoir 3 nearby the beads by aspirate-blow action for 100 times
26. Lower down magnet strip. Keep heating block at room temperature (about 23±2° C.). Transfer 60 ul of elution buffer from elution buffer chamber and add to reaction reservoir 3 to elute nucleic acid by aspirate-blow action for 250 times in 10 minute.
27. Wash liquid tip 6 times with Tip wash buffer
28. Elevate magnet strip to attract beads and transfer 60 ul of eluted and converted nucleic acid in supernatant (eluent) to 1.5 ml collection tube
29. Remove liquid tip.

II. Evaluation of Patient Samples for Colorectal Cancer Markers

Samples were manually prepared using the Epi proColon Sensitive PCR Kit (M5-02-002) and the Epi proColon Control Kit (M5-02-003) according to manufacturer's directions.

Each bisulfite converted DNA sample (bisDNA) (patient sample, or Epi proColon Positive Control, or Epi proColon Negative Control) must be tested in triplicate.

TABLE 1

Thermal Cycler Program for Applied Biosystems 7500 Fast/Fast Dx

| Program Parameter | Denaturation | Cycling | | | Holding |
|---|---|---|---|---|---|
| Stage | "Stage 1" | "Stage 2" | | | "Stage 3" |
| Repetitions | 1 | 45 | | | 1 |
| Step | 1 | 1 | 2 | 3 | 1 |
| Target [° C.] | 94 | 62 | 55.5 | 93 | 40 |
| Hold [mm:ss] | 20:00 | 00:05 | 00:35 | 00:30 | 00:05 |
| Auto Increment | | 0 | 0 | 0 | |
| Ramp Rate [%] | 40 | 80 | 80 | 40 | 80 |
| Data Collection | | Stage 2, Step 2 (55.5 @ 0:35) | | | |

Result of Comparison:

| Sample | Positive Control | Positive Control | Negative Control | Negative Control | Clinical Sample | Clinical Sample |
|---|---|---|---|---|---|---|
| Target Gene | Septin9 | Actin | Septin9 | Actin | Septin9 | Actin |
| Ct of Manual Method | 36.12 | 29.5 | NA | 33.45 | 36.39 | 27.27 |
| Ct of Automation | 36.25 | 29.12 | NA | 32.72 | 36.7 | 26.9 |

Ct results from Manual Method and from Automated Sample Preparation System to prepare methylated nucleic acid are similar to each other. Both methods have obtained similar results that indicate that Automated Sample Preparation System for Methylated Nucleic Acids can be an alternative method or better method for Sample Preparation for Methylated Nucleic Acids other than manual method Those having ordinary skill in the art will understand that many modifications, alternatives, and equivalents are possible. All such modifications, alternatives, and equivalents are intended to be encompassed herein.

While the principles of this invention have been described in connection with specific embodiments, it can be understood clearly that these descriptions are made only by way of example and are not intended to limit the scope of the invention. What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalence.

What is claimed:

1. A method for performing sequential nucleic acid isolation and conversion/purification reaction(s) in a closed automated device which includes:
   (A) a plurality of reaction reservoirs;
   (B) a heating unit configured to heat the plurality of reaction reservoirs;
   (C) a magnet configured to be elevated and lowered relative to the reaction reservoirs;
   the method comprising:
   a. contacting the nucleic acid-containing sample with an extraction reagent in a first reservoir of the plurality of the reaction chambers to thereby extract the nucleic acid from the sample;
   b. binding the extracted nucleic acid with a first plurality of magnetic beads in the first reservoir;
   c. while holding the magnetic beads down by elevating the magnet relative to the first plurality of magnetic beads, removing liquid supernatant formed in the first reservoir;
   d. eluting the bound extracted nucleic acid from the first plurality of magnetic beads using a first elution buffer while subjecting the first reservoir to a first elevated temperature by the heating unit for a first predetermined duration of time to thereby obtain an isolated nucleic acid eluent;
   e. while holding the magnetic beads down by elevating the magnet relative to the first plurality of magnetic beads, transferring the isolated nucleic acid eluent to a second reservoir of the plurality of reaction reservoirs, the second reaction reservoir containing a conversion reagent;
   f. reacting said isolated nucleic acid with the conversion reagent in the second reservoir while subjecting the second reservoir to a second elevated temperature by the heating unit for a second predetermined duration of time, to thereby obtain a modified nucleic acid;
   g. binding the modified nucleic acid with a second plurality of magnetic beads;
   h. while holding the magnetic beads down by elevating the magnet relative to the second plurality of magnetic beads, removing liquid supernatant formed;
   j. eluting the bound modified nucleic acid from the second plurality of magnetic beads using a second elution buffer or a second series of elution buffers to thereby obtain a purified modified nucleic acid eluent.

2. The method of claim 1, wherein said conversion is methylation.

3. The method of claim 2, wherein the methylation comprises bisulfite conversion.

4. The method of claim 3, wherein the bisulfite conversion is a deamination of cytosine into uracil of said isolated nucleic acid.

5. The method of claim 3, wherein the conversion reagent comprises bisulfite.

6. The method of claim 3, further comprising a step of desulfonation.

7. The method of claim 1, wherein the sample is selected from the group consisting of whole blood, plasma, serum, buffy coat, saliva, cheek swab, sputum, stool, urine, cerebral spinal fluid, a cell, a tissue and a formalin fixed paraffin embedded (FFPE) sample.

8. The method of claim 1, wherein the nucleic acid is DNA, RNA, cDNA or a combination thereof.

* * * * *

SEQUENCE LISTING

<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: Demo of mechanism for detecting methylation.

<400> SEQUENCE: 1
tgcgcaagcg catgccgct                                              19

<210> SEQ ID NO 2
<211> LENGTH: 19
<212> TYPE: DNA
<213> ORGANISM: Artificial Sequence
<220> FEATURE:
<223> OTHER INFORMATION: Demo of mechanism for detecting methylation.

<400> SEQUENCE: 2
tgcguaagcg uatgucgut                                              19

```
<210> SEQ ID NO 3
<211> LENGTH: 19
<212> TYPE: DNA
<213> ORGANISM: Artificial Sequence
<220> FEATURE:
<223> OTHER INFORMATION: Demo of mechanism for detecting methylation.

<400> SEQUENCE: 3
acgcgttcgc gtacggcga                                                19

<210> SEQ ID NO 4
<211> LENGTH: 19
<212> TYPE: DNA
<213> ORGANISM: Artificial Sequence
<220> FEATURE:
<223> OTHER INFORMATION: Demo of mechanism for detecting methylation.

<400> SEQUENCE: 4
augcgttugc gtauggcga                                                19
```